(12) United States Patent
Bowman et al.

(10) Patent No.: US 9,104,656 B2
(45) Date of Patent: Aug. 11, 2015

(54) USING LEXICAL ANALYSIS AND PARSING IN GENOME RESEARCH

(75) Inventors: Stephen D. Bowman, Monroe, NC (US); Dandala V. Reddy, Apex, NC (US); David B. Werts, Charlotte, NC (US)

(73) Assignee: International Business Machines Corporation, Armonk, NY (US)

( * ) Notice: Subject to any disclaimer, the term of this patent is extended or adjusted under 35 U.S.C. 154(b) by 163 days.

(21) Appl. No.: 13/541,475

(22) Filed: Jul. 3, 2012

(65) Prior Publication Data

US 2014/0012865 A1    Jan. 9, 2014

(51) Int. Cl.
| | |
|---|---|
| *G06F 7/00* | (2006.01) |
| *G06F 17/30* | (2006.01) |
| *G01N 33/48* | (2006.01) |
| *G01N 33/50* | (2006.01) |
| *G06F 17/27* | (2006.01) |
| *G06F 19/22* | (2011.01) |
| *G06F 19/18* | (2011.01) |
| *G06F 19/24* | (2011.01) |
| *G06F 15/16* | (2006.01) |

(52) U.S. Cl.
CPC ...... *G06F 17/2705* (2013.01); *G06F 17/30634* (2013.01); *G06F 19/18* (2013.01); *G06F 19/22* (2013.01); *G06F 19/24* (2013.01)

(58) Field of Classification Search
CPC .............................. G06F 17/2705; G06F 19/22
USPC ....................................... 707/755; 702/20, 19
See application file for complete search history.

(56) References Cited

U.S. PATENT DOCUMENTS

| | | | |
|---|---|---|---|
| 6,553,385 B2 | 4/2003 | Johnson et al. | |
| 7,139,752 B2 | 11/2006 | Broder et al. | |
| 7,428,554 B1 | 9/2008 | Coberley et al. | |
| 7,512,602 B2 | 3/2009 | Broder et al. | |
| 7,558,778 B2 | 7/2009 | Carus et al. | |
| 8,086,409 B2 | 12/2011 | Anastassiou et al. | |
| 2002/0168664 A1 * | 11/2002 | Murray et al. | 702/20 |
| 2004/0243556 A1 | 12/2004 | Ferrucci et al. | |

(Continued)

FOREIGN PATENT DOCUMENTS

JP    2004030093 A    1/2004

OTHER PUBLICATIONS

Sabita Barik et al.; "Discovery using Fuzzy FP-growth Algorithm from Gene Expression Data"; International Journal of Advanced Computer Science and Applications ( IJACSA), vol. 1, No. 5, Nov. 2010; Publisher: Institute of Technical Education and Research, India, Total 6 pp.

(Continued)

*Primary Examiner* — Usmaan Saeed
*Assistant Examiner* — Brian E. Weinrich
(74) *Attorney, Agent, or Firm* — Janaki K. Davda; Konrad, Raynes, Davda and Victor LLP

(57) ABSTRACT

Provided are techniques for locating one or more genome patterns. One or more lexical annotators that each identifies a sequence of nucleotides are created. One or more parsing rule annotators are created using at least one of (1) one or more of the lexical annotators, (2) one or more dictionary entries, and (3) one or more previously-defined parsing rule annotators. The one or more parsing rule annotators are used to discover the one or more genome patterns comprising a combination of the lexical annotators and the parsing rule annotators.

14 Claims, 15 Drawing Sheets

(56) References Cited

U.S. PATENT DOCUMENTS

| | | | | |
|---|---|---|---|---|
| 2004/0243645 | A1* | 12/2004 | Broder et al. | 707/999.2 |
| 2007/0054277 | A1* | 3/2007 | Evans | 702/20 |
| 2008/0243397 | A1* | 10/2008 | Peccoud et al. | 702/20 |
| 2009/0254572 | A1* | 10/2009 | Redlich et al. | 707/999.107 |
| 2010/0169234 | A1* | 7/2010 | Metzger et al. | 705/348 |
| 2012/0102041 | A1* | 4/2012 | Park et al. | 707/741 |
| 2012/0102054 | A1* | 4/2012 | Popescu et al. | 707/755 |
| 2013/0073571 | A1* | 3/2013 | Coulet et al. | 707/755 |
| 2013/0254218 | A1* | 9/2013 | Friedlander et al. | 707/755 |

OTHER PUBLICATIONS

English Abstract & Translation for JP2004030093A, published Jan. 29, 2004, Total 18 pp.

Mell, P. and T. Grance, "Effectively and Securely Using the Cloud Computing Paradigm", [online], Oct. 7, 2009, retrieved from the Internet at <URL: http://csrc.nist.gov/groups/SNS/cloud-computing/cloud-computing-v26.ppt>, Total 80 pp.

Mell, P. and T. Grance, "The NIST Definition of Cloud Computing (Draft)", Jan. 2011, Computer Security Division Information Technology Laboratory National Institute of Standards and Technology, Total 7 pp.

US Patent Application, for U.S. Appl. No. 13/875,713, filed May 2, 2013, entitled, "Using Annotators in Genome Research", invented by Stephen D. Bowman et al., pp. 1-39.

Preliminary Remarks, dated May 2, 2013, for U.S. Appl. No. 13/875,713, filed May 2, 2013, entitled. "Using Annotators in Genome Research", invented by Stephen D. Bowman et al., pp. 1-5.

Final Office Action, dated Aug. 21, 2014, for U.S. Appl. No. 13/875,713 (54.80C1), filed May 2, 2013, invented by Stephen D. Bowman et al., Total 21 pages.

Response to Final Office Action, dated Nov. 20, 2014, for U.S. Appl. No. 13/875,713 (54.80C1), filed May 2, 2013, invented by Stephen D. Bowman et al., Total 12 pages.

Office Action, dated Feb. 28, 2014, for U.S. Appl. No. 13/875,713 (54.80C1), filed May 2, 2013, entitled, "Using Annotators in Genome Research", invented by Stephen D. Bowman et al., Total 21 pages.

Response to Office Action, dated May 27, 2014, for U.S. Appl. No. 13/875,713 (54.80C1), filed May 2, 2013, entitled, "Using Annotators in Genome Research", invented by Stephen D. Bowman et al., Total 13 pages.

Office Action, dated Dec. 15, 2014, for U.S. Appl. No. 13/875,713 (54.80C1), filed May 2, 2013, invented by Stephen D. Bowman et al., Total 22 pages.

Response to Office Action, dated Mar. 18, 2015, for U.S. Appl. No. 13/875,713 (54.80C1), filed May 2, 2013, invented by Stephen D. Bowman et al., Total 8 pages.

Notice of Allowance, dated Apr. 6, 2015, for U.S. Appl. No. 13/875,713, filed May 2, 2013, invented by Stephen D. Bowman et al., Total 10 pages.

* cited by examiner

AGCTTTCCGCGAGAAAACAGTACAGGTCCGAGTAGGTCTTTCAGAAACAGT
ACAGGAGGTCT...

FIG. 6
SEQ ID NO:1:

FIG. 7
SEQ ID NO:1:

AGCCTTTCCGCCGGAGAAACAGTACAGGTCCGAGTAGGTCTTTCAGAAACAGT
ACAGGAGGTCT...

702
600

AGCTTTCCGCGAGAAACAGTACAGGTCCGAGTAGGTCTTTCAGAAACAG
TACAGGAGGTCT...

600

902

FIG. 9
SEQ ID NO:1:

1100

```
ANALYSIS TEXT:
AGCTTTCCGCGAGAAACAGTACAGGTCCGAGTAGGT
CTTTCAGAAACAGTACAGGAGGTCT...
----------------------------------------------------------------
LANGUAGE:
English
ANNOTATIONS:
document:
start position 0, end position 12345
paragraph:
start position 0, end position 12345
token:
start position 0, end position 0
start position 1, end position 1
start position 2, end position 2
...
start position 12345, end position 12345.
```

FIG. 11
SEQ ID NO:1:

1200

```
ANALYSIS TEXT:
A G C T T T C C G C G A G A A A C A G T A C A G G T C C G A G T A G G T
C T T T C A G A A A C A G T A C A G G A G G T C T...
------------------------------------------------------------------
LANGUAGE:
English
ANNOTATIONS:
document annotation:
start position 0, end position 12345
paragraph annotation:
start position 0, end position 12345
token annotation:
start position 0, end position 0
start position 1, end position 1
start position 2, end position 2
...
start position 12345, end position 12345
SequenceG annotation:
start position 12, end position 16
start position 42, end position 46
start position 1002, end position 1006
...
SequenceR annotation:
start position 2, end position 6
start position 36, end position 40
start position 4002, end position 4006
...
```

FIG. 12
SEQ ID NO:1:

1300

ANALYSIS TEXT:
A G C T T T C C G C G A G A A A C A G T A C A G G T C C G A G T A G G T
C T T T C A G A A A C A G T A C A G G A G G T C T...
------------------------------------------------------------------------
LANGUAGE:
English
ANNOTATIONS:
document annotation:
start position 0, end position 12345
paragraph annotation:
start position 0, end position 12345
token annotation:
start position 0, end position 0
start position 1, end position 1
start position 2, end position 2
...
start position 12345, end position 12345
SequenceG annotation:
start position 12, end position 16
start position 42, end position 46
start position 1002, end position 1006
...
SequenceR annotation:
start position 2, end position 6
start position 36, end position 40
start position 4002, end position 4006
...
SequenceRAG annotation:
start position 36, end position 46

FIG. 13
SEQ ID NO:1:

ANALYSIS TEXT:
A G C T T T C C G C G A G A A A C A G T A C A G G T C C G A G T A G G T
C T T T C A G A A A C A G T A C A G G A G G T C T...
---------------------------------------------------------------------
LANGUAGE:
English
ANNOTATIONS:
document annotation:
start position 0, end position 12345
paragraph annotation:
start position 0, end position 12345
token annotation:
start position 0, end position 0
start position 1, end position 1
start position 2, end position 2

...

start position 12345, end position 12345
SequenceG annotation:
start position 12, end position 16
start position 42, end position 46
start position 1002, end position 1006

...

SequenceR annotation:
start position 2, end position 6
start position 36, end position 40
start position 4002, end position 4006

...

SequenceRAG annotation:
start position 36, end position 46

FIG. 14
SEQ ID NO:1:

AGCTTTCCGCCGAGAAACAGTACAGGTCCGAGTAGGTCTTTCAGAAACAGT
ACAGGAGGTCT...

600

1502

FIG. 15
SEQ ID NO:1:

SEQUENCE LISTING

```
<160> NUMBER OF SEQ ID NOS: 1

<210> SEQ ID NO 1
<211> LENGTH: 61
<212> TYPE: DNA
<213> ORGANISM: Artificial Sequence
```

```
<220> FEATURE:
<223> OTHER INFORMATION: random sequence used by inventors to illustrate
      embodiments of the invention

<400> SEQUENCE: 1
agctttccgc gagaaacagt acaggtccga gtaggtcttt cagaaacagt acaggaggtc      60
t                                                                     61
```

USING LEXICAL ANALYSIS AND PARSING IN GENOME RESEARCH

SEQUENCE LISTING

A text file (named SVL920120009US1_Text_File) containing a sequence listing is incorporated by reference herein in its entirety. The name of the text file is SVL920120009US1_Text_File, the date of creation of the text file is Sep. 10, 2012, and the size of the text file in bytes is 1 KB.

Using this coding mechanism of A, C, G, and T, genetic sequences may be documented in a simple form such as:

```
SEQ ID NO: 1:
...AGCTTTCCGCGAGAAACAGTACAGGTCCGAGTAGGTCTTTC

AGAAACAGTACAGGAGGTCT...
```

FIELD

Embodiments of the invention relate to using annotators in genome research.

BACKGROUND

The Human Genome Project may be described as an international scientific research project with a primary goal of sequencing and mapping all of the genes—together known as the genome—of humans. The Human Genome Project involves identifying and mapping approximately 20,000-25,000 genes of the human genome.

The Human Genome Project has provided advancements in the study and understanding of human Deoxyribonucleic Acid (DNA). DNA may be described as a nucleic acid containing the genetic instructions used in the development and functioning of most known living organisms. The DNA segments carrying this genetic information are called genes. Valuable research is still coming out of this work, especially around gene sequencing and genomic annotation. However, the resource costs involved in such genomic research are high, whether measuring time, effort, or money.

SUMMARY

Provided are a method, computer program product, and system for locating one or more genome patterns. One or more lexical annotators that each identify a sequence of nucleotides are created. One or more parsing rule annotators are created using at least one of (1) one or more of the lexical annotators, (2) one or more dictionary entries, and (3) one or more previously-defined parsing rule annotators. The one or more parsing rule annotators are used to discover the one or more genome patterns comprising a combination of the lexical annotators and the parsing rule annotators.

BRIEF DESCRIPTION OF THE SEVERAL VIEWS OF THE DRAWINGS

Referring now to the drawings in which like reference numbers represent corresponding parts throughout:

FIG. 6 illustrates selection of a first character sequence in an example genetic sequence in accordance with certain embodiments.

FIG. 7 illustrates selection of a second character sequence in an example genetic sequence in accordance with certain embodiments.

FIG. 9 illustrates a matched pattern in an example genetic sequence in accordance with certain embodiments.

FIG. 11 illustrates a logical representation of a Common Analysis Structure (CAS) after a first UIMA stage in accordance with certain embodiments.

FIG. 12 illustrates a logical representation of a CAS after a second UIMA stage in accordance with certain embodiments.

FIG. 13 illustrates a logical representation of a CAS after a third UIMA stage in accordance with certain embodiments.

FIG. 14 illustrates a logical representation of a CAS after a fourth UIMA stage in accordance with certain embodiments.

FIG. 15 illustrates a matched pattern in an example genetic sequence in accordance with certain embodiments.

DETAILED DESCRIPTION

Figure 1:
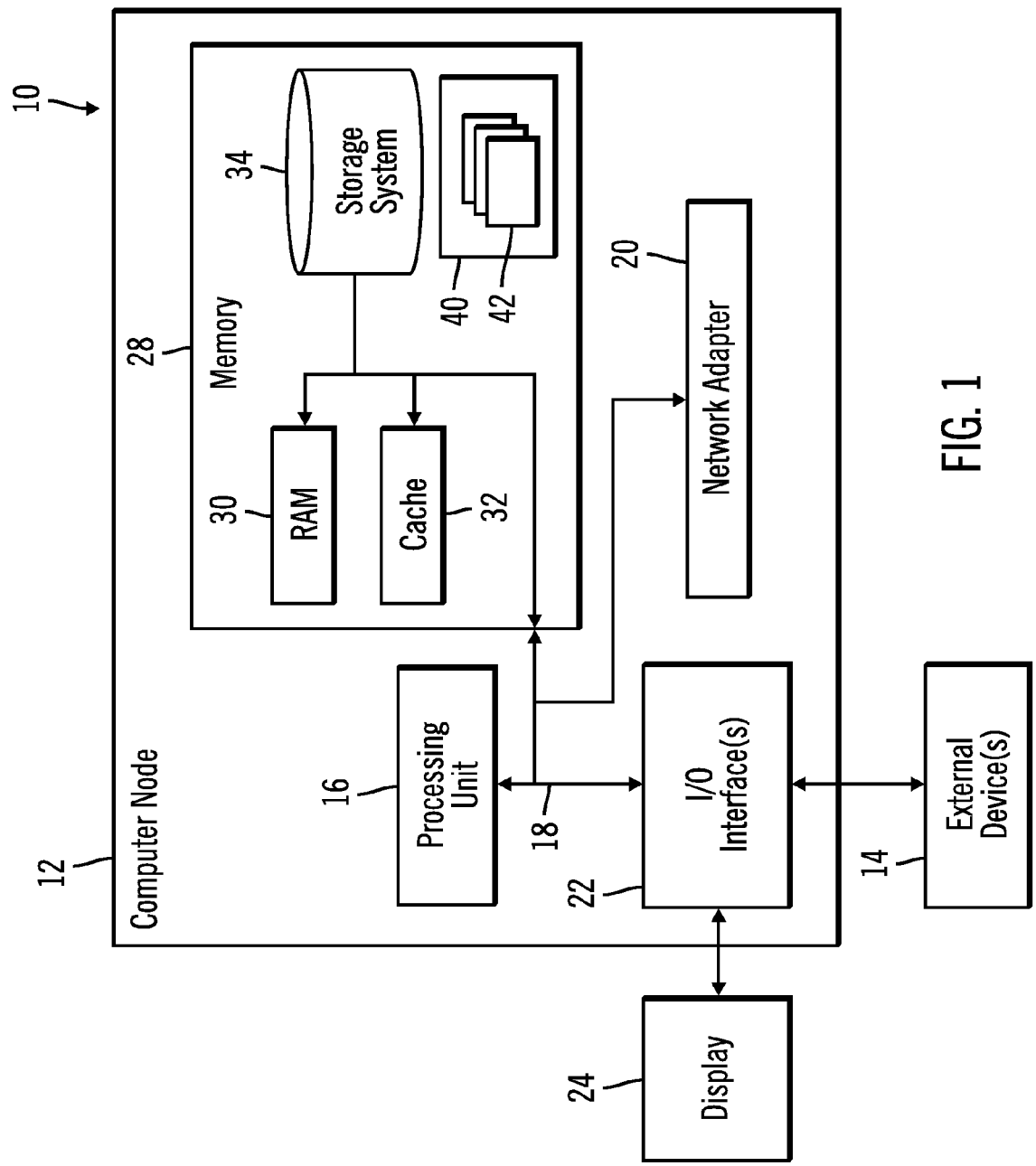
FIG. 1 depicts a cloud computing node in accordance with certain embodiments.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
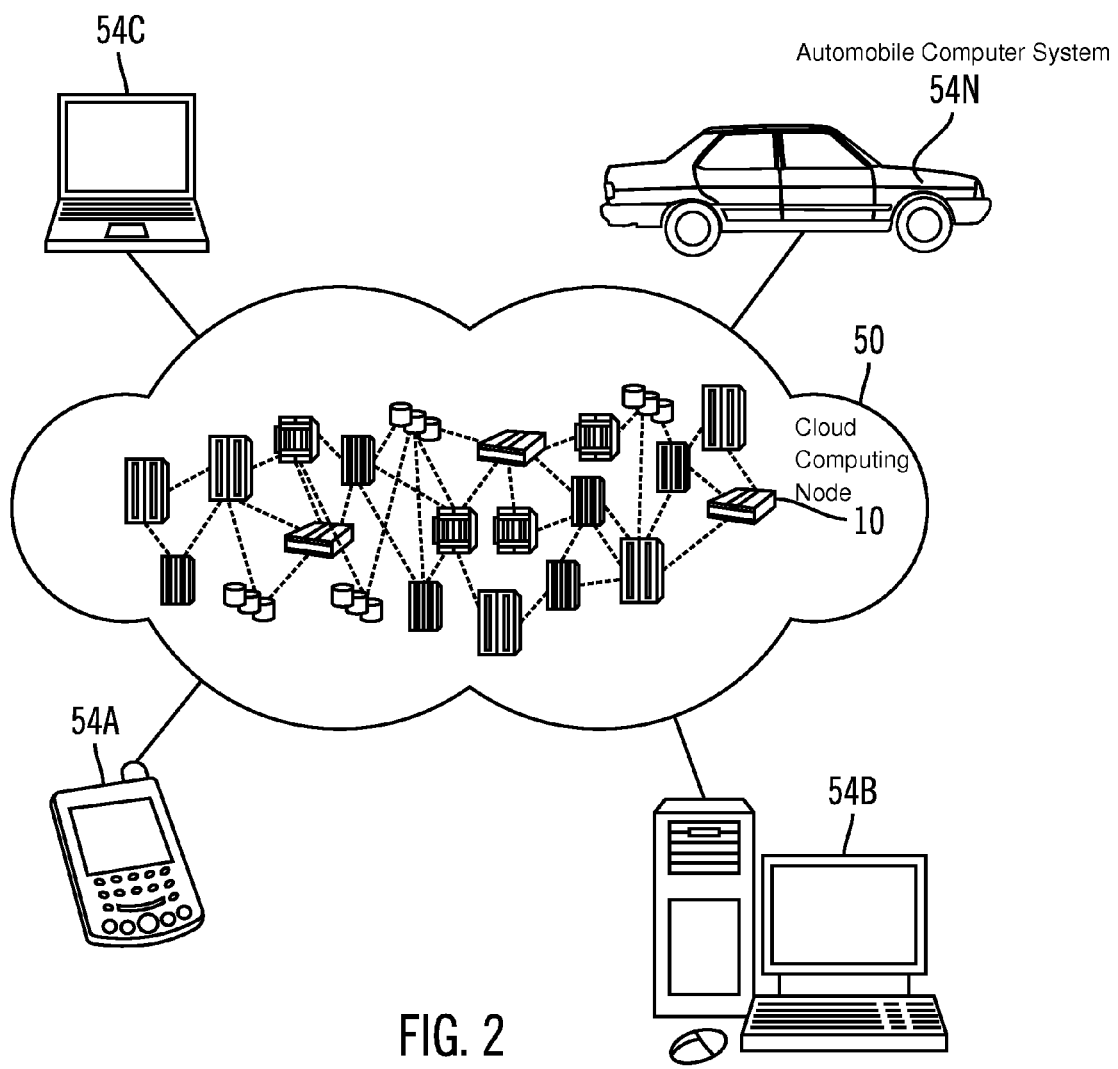
FIG. 2 depicts a cloud computing environment in accordance with certain embodiments.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
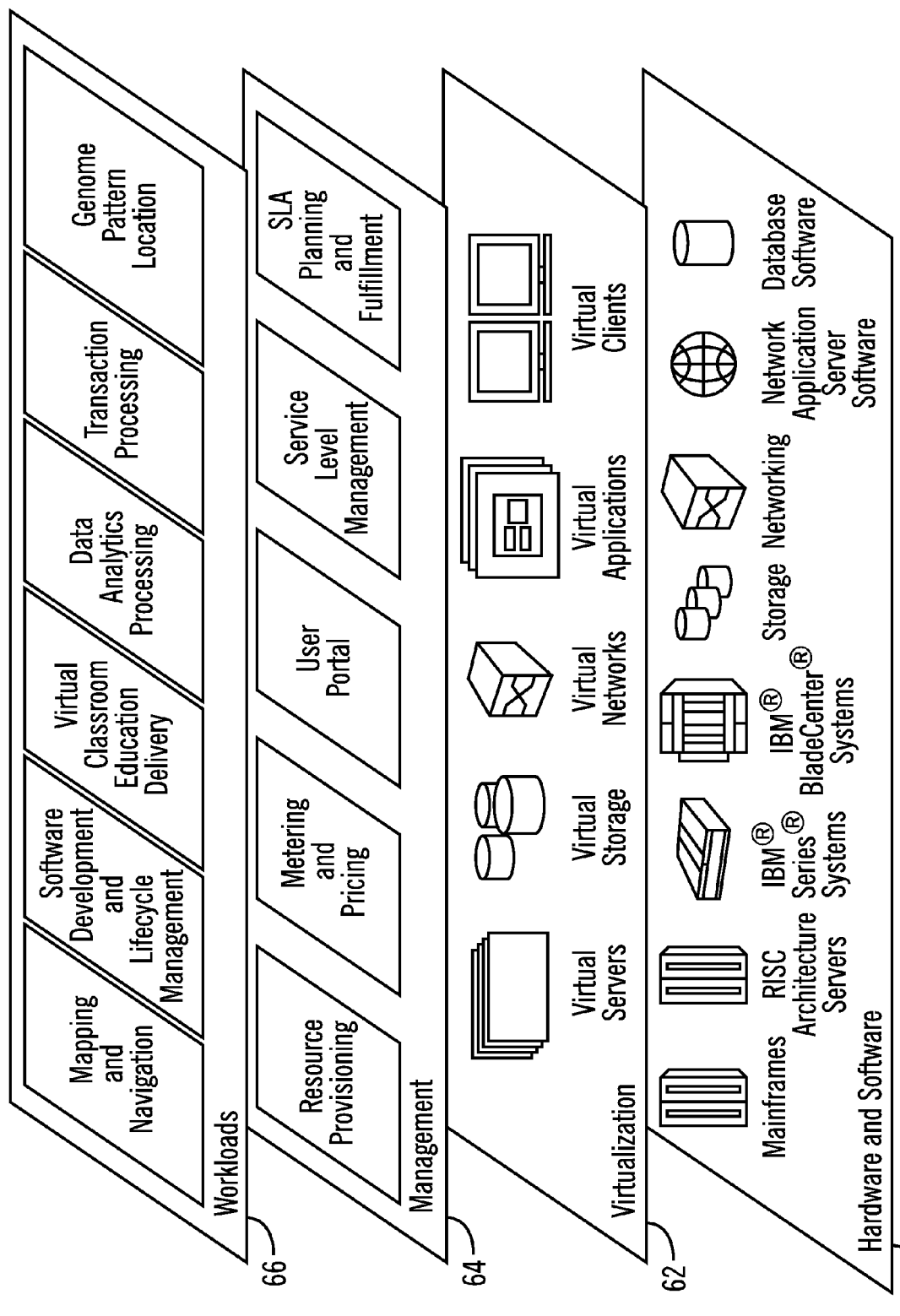
FIG. 3 depicts abstraction model layers in accordance with certain embodiments.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Hardware and software layer 60 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 62 provides an abstraction layer from which the following examples of virtual entities may be provided: virtual servers; virtual storage; virtual networks, including virtual private networks; virtual applications and operating systems; and virtual clients.

In one example, management layer 64 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 66 provides examples of functionality for which the cloud computing environment may be utilized. Examples of workloads and functions which may be provided from this layer include: mapping and navigation; software development and lifecycle management; virtual classroom education delivery; data analytics processing; transaction processing; and genome pattern location.

Thus, in certain embodiments, software, implementing genome pattern location in accordance with embodiments described herein, is provided as a service in a cloud environment.

Figure 4:
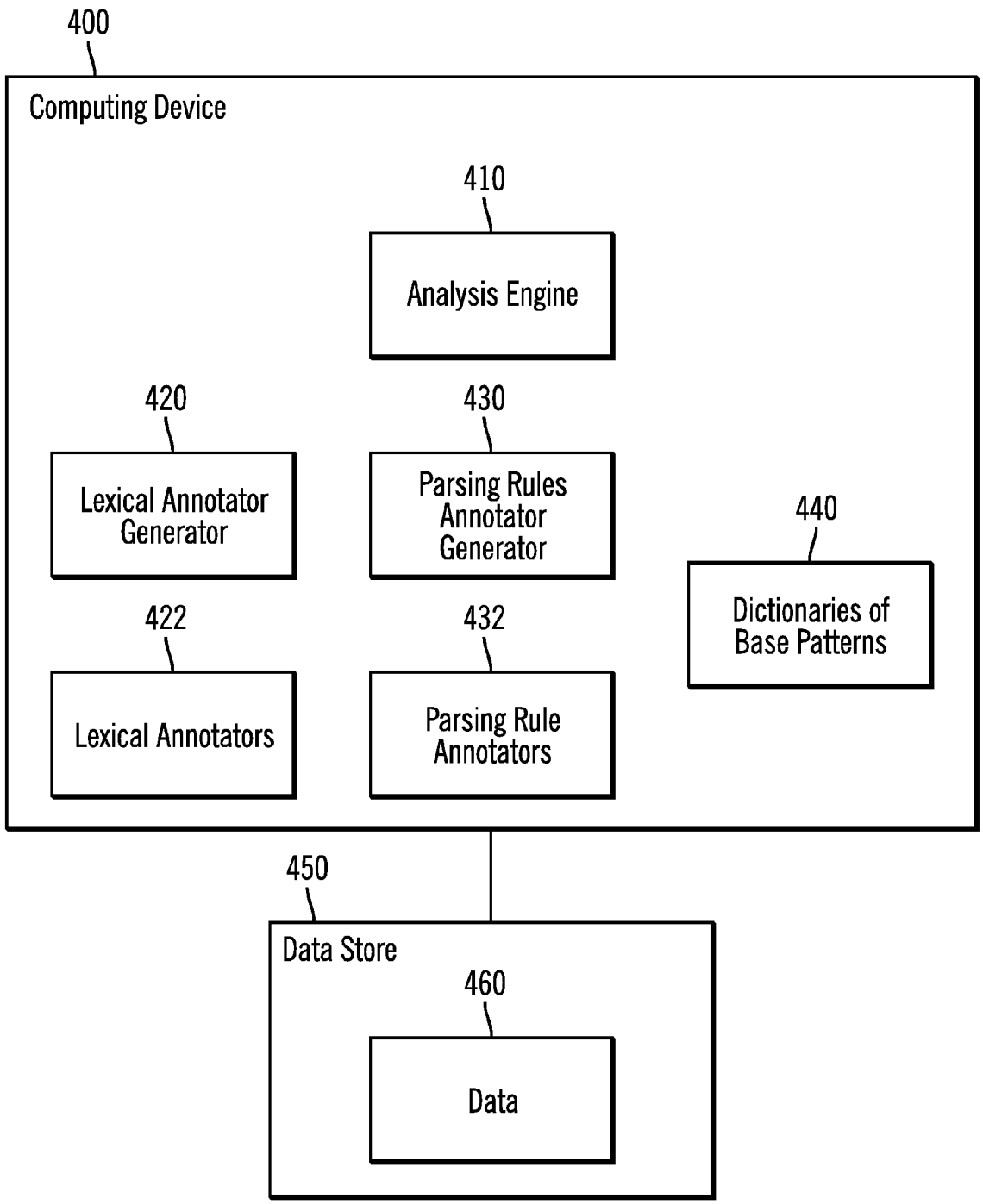
FIG. 4 illustrates a computing environment in accordance with certain embodiments.

FIG. 4 illustrates a computing environment in accordance with certain embodiments. A computing device 400 includes an analysis engine 410, a lexical annotator generator 420, and a parsing rule annotator generator 430. The lexical annotator generator 420 enables a user (e.g., a researcher) to create and edit one or more lexical annotators 422 by selecting (e.g., entering via an input device or a user interface) a sequence of characters. The parsing rule annotator generator 430 enables a user to create and edit one or more parsing rule annotators 432 by selecting (e.g., entering via an input device or a user interface) any combination of a sequence of characters, dictionary entries (from the dictionaries of base patterns 440), lexical annotators 442, and/or previously-defined parsing rule annotators 432. The computing device 400 also includes one or more dictionaries of base patterns 440. A character rule may be described as a type of lexical annotator 422. In certain embodiments, the lexical annotator generator 420 is an editor. In certain embodiments, the parsing rule annotator generator 430 is an editor.

The computing device 400 is coupled to a data store 450. The data store 450 stores data 460.

In certain embodiments, the computing device 400 has the architecture of computing node 10. In certain embodiments, the computing device 400 is part of a cloud environment. In certain alternative embodiments, the computing device 400 is not part of a cloud environment.

A genome is composed of chromosomes which, in turn, package genes. Genes are made up of DNA molecules, and these DNA molecules are composed of nucleotides. Sequences of nucleotides are noted in a very simple code representing their bases: adenine (A), cytosine (C), guanine (G), and thymine (T).

Unstructured Information Management Architecture (UIMA) pipelines. UIMA may be described as a software architecture for the use of analytics for the analysis of unstructured information. The lexical annotator generator 420 and the parsing rule annotator generator 430 are used to build custom text analytics annotators for UIMA pipelines. Text analytics is used in environments in which linguistic grammars, dictionaries, and parsing rules are utilized to help tease meaning from text sources. Annotator may be described as a collection of character and/or parsing rules that are related in some way. The UIMA framework uses these annotators to help find matches in the text being analyzed. When a match is found (i.e., when an annotator rule is satisfied), an annotation is recorded in a Common Analysis Structure (CAS) that identifies the match, its location in the text, etc. Thus, the annotator is a tool to help find matches. An annotation may be described as the match that has been found and noted in the CAS.

The analysis engine 410 enables users to discover genomic information based on nucleotide sequences and relationships by the use of custom UIMA annotators. These custom annotators can then be used to help locate various genes in the sequence, to help figure out what these genes do, to help determine how they are related to each other, etc. Further, variations in a sequence can be discovered that may offer clues to disease and/or cancer research. Since these discoveries can be made against genetic sequences documented in the code representing nucleotide bases A, C, G, and T, without special-use hardware, the costs in time, effort, and money is reduced.

Using this coding mechanism of A, C, G, and T, genetic sequences may be documented in a simple form such as:

```
. . . AGCTTTCCGCGAGAAACAGTACAGGTCCGAGTAGGTCTTTCAG

AAACAGTACAGGAGGTCT . . .
```

The analysis engine 410, the lexical annotator generator 420, and the parsing rule annotator generator 430 are used to create custom annotators capable of extracting various pieces of information from the approximately 3 billion bases that make up the genetic sequence of humans. These custom annotators can then be used to help locate various genes in the sequence, to help figure out what these genes do, to help determine how they are related to each other, etc. Further, by defining lexical annotators 422 and dictionaries of base patterns 440 describing various genes, and by building parsing rule annotators 432 around these base patterns, the embodiments help locate variations in genes that may offer clues to disease and/or cancer research. The dictionaries of base patterns 440 have dictionary entries.

In certain embodiments, the dictionaries of base patterns 440 are lists of "words" that have been chosen to mean something in terms of lexical analysis. As a general example, there may be a "dictionary of First Names" that includes a list of names that are to be identified (i.e., annotated) as a "First Name" annotation. The dictionary of First Names may include "Janaki," "Blake," "Stephen," and "Vinod" as first name entries. During the lexical analysis phase, when any tokens (e.g., words) are "matched" to entries in a dictionary of base patterns 440, the token is annotated in the CAS (e.g., with an indication that there is a First Name match). In the genome space, there may be a dictionary of nucleotide sequences that are to be annotated when matches are found. As a simple example, a dictionary of nucleotide sequences may give some indication of eye color or hair color, etc.

Examples will be provided herein with reference to an example genetic sequence 600 (illustrated in FIG. 6) merely to enhance understanding of embodiments. Suppose a user hypothesizes that a specific sequence of genes occurring together increases the risk one may have towards an ailment later in life. The lexical annotator generator 420 is used to build lexical annotators 422 to match each gene sequence (or gene markers) in question, then, those possible annotations are used in parsing rule annotators 432 created by the parsing rule annotator generator 430. The analysis engine 410 then determines whether or not a particular sequence can be found in a set of genome sequence maps.

Figure 5:
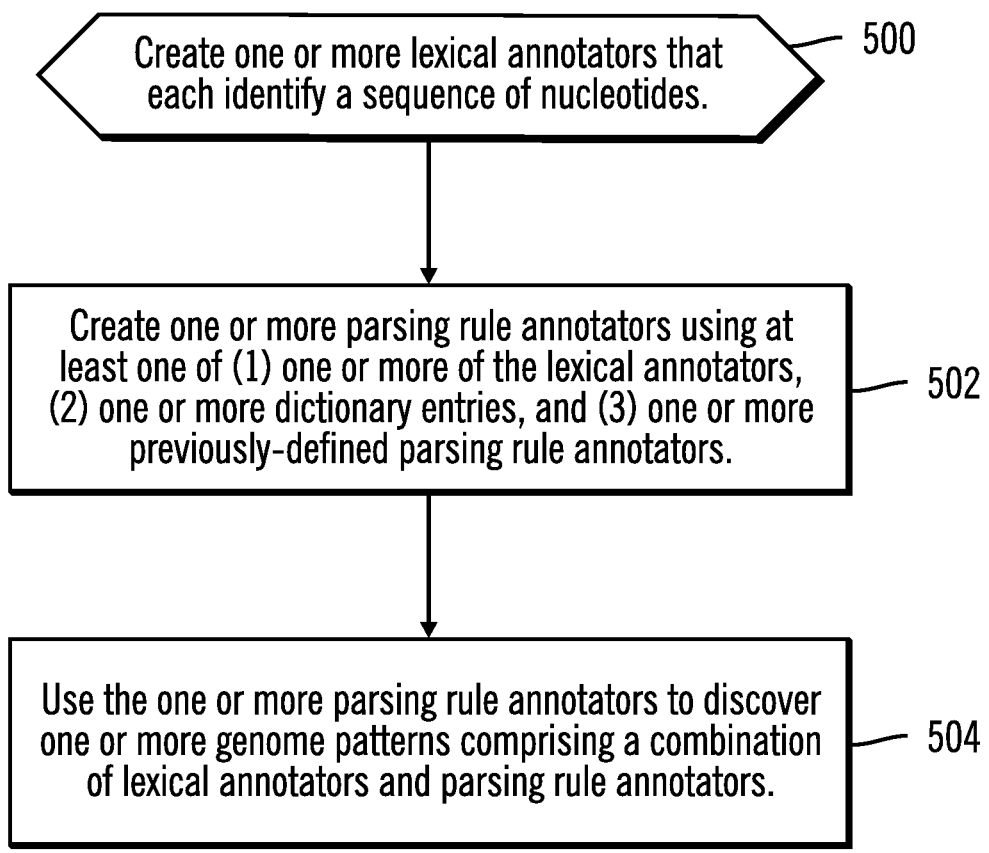
FIG. 5 illustrates, in a flow diagram, operations performed to locate a genome pattern in analytic text in accordance with certain embodiments.
Figure 6:
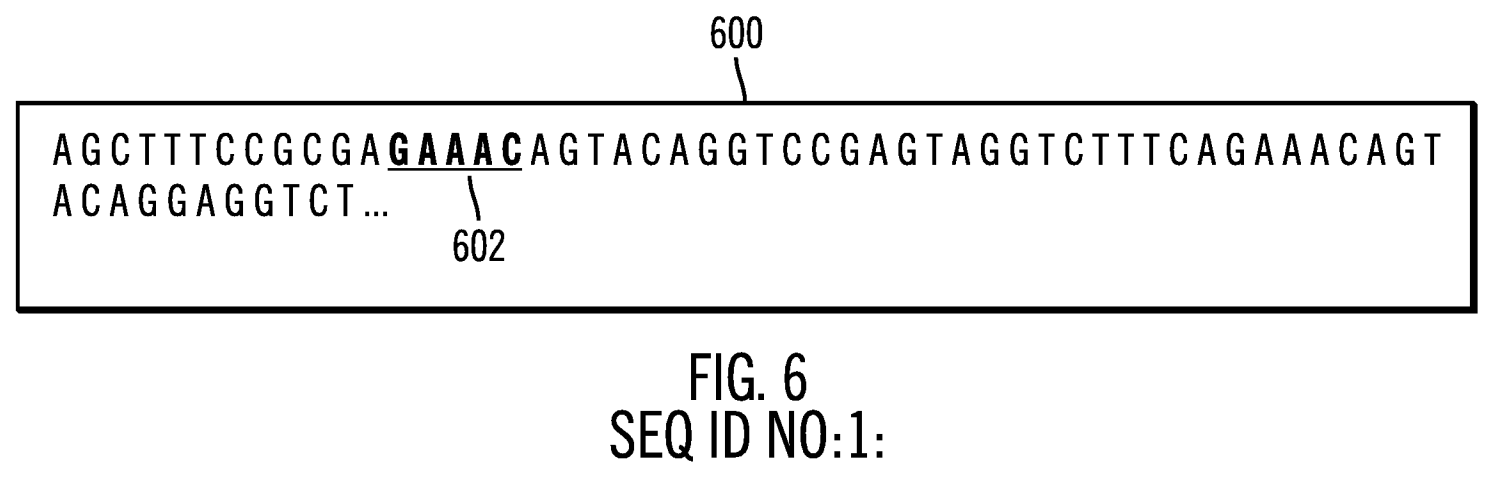

FIG. 5 illustrates, in a flow diagram, operations performed to locate a genome pattern in analytic text in accordance with certain embodiments. Control begins in block at block 500 with creating one or more lexical annotators that each identifies a sequence of nucleotides. In particular, using the lexical annotator generator 420, a user selects a sequence of characters ("character sequence") that is used to create a new lexical annotator 422. FIG. 6 illustrates selection of a first character sequence 602 in an example genetic sequence 600 in accordance with certain embodiments. In FIG. 6, characters GAAAC are selected (e.g., highlighted) to build a new lexical annotator 422. In FIG. 6, the character sequence GAAAC is shown underlined. Once the character sequence GAAAC is selected, the lexical annotator generator 420 creates a lexical annotator 422 that creates an annotation called "SequenceG" when a match is found on this character sequence.

Continuing with the example genetic sequence 600, the user is looking to see whether a combination of nucleotide sequences occurs. Therefore, the user uses the lexical annotator generator 420 to select a second set of characters (i.e., another character sequence) that is used to create another, new lexical annotator 422. FIG. 7 illustrates selection of a second character sequence 702 in an example genetic sequence 600 in accordance with certain embodiments. In FIG. 7, characters CTTTC are selected (e.g., highlighted) to build a new lexical annotator 422. In FIG. 7, the character sequence CTTTC is shown underlined. Once the character sequence CTTTC is selected, the lexical annotator generator 420 creates a lexical annotator 422 that creates an annotation called "SequenceR" when a match is found in this character sequence.

In block 502, one or more parsing rule annotators 432 are created using at least one of (1) one or more of the lexical annotators 422, (2) one or more dictionary entries from the one or more dictionaries of base patterns 440, and one or more previously-defined parsing rule annotators. Continuing with the example genetic sequence 600, using the parsing rule annotator generator 430, a user creates parsing rule annotators 432 around annotations generated by any of the lexical annotators 422 that have been created. Embodiments provide many options for building complex parsing rule annotators 432 using these lexical annotators 422, dictionary entries, and previously-defined parsing rule annotators 432. The parsing rule annotators 432 may be based on proximity, order, and other rules. For example, a user may look for instances where different annotations appear within a span of 100 or less nucleotides of each other. Another example would be that the user looks for the absence of one annotation in relation to another annotation (e.g., locate a sequence of nucleotides where SequenceR is NOT within 200 nucleotide markers of a SequenceG annotation).

Figure 8:
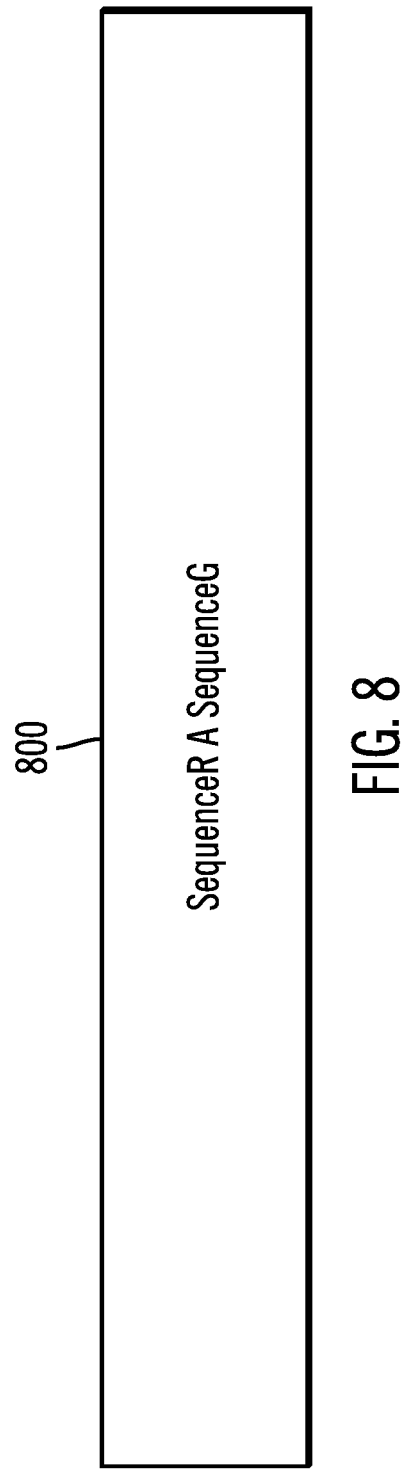
FIG. 8 illustrates an example parsing rule annotator in accordance with certain embodiments.

Continuing with the example genetic sequence 600, the user is interested in seeing whether there exist any instances in which the SequenceR annotation is followed by the adenine (A) nucleotide and then followed by the SequenceG annotation. FIG. 8 illustrates an example parsing rule 800 in accordance with certain embodiments. The new parsing rule 800 creates an annotation called "SequenceRAG" when a match is found in any analytic text in which the characters that make up the SequenceR annotation is followed by the nucleotide "A" followed by the characters that make up the SequenceG annotation.

In block 504, the analysis engine 410 uses the one or more parsing rule annotators 432 to discover one or more genome patterns comprising a combination of the lexical annotators 422 and the parsing rule annotators 432. In certain embodiments, the combination of the lexical annotators 422 and the parsing rule annotators 432 includes only lexical annotators 422. In certain embodiments, the combination of the lexical annotators 422 and the parsing rule annotators 432 includes only the parsing rule annotators 432. Continuing with the example genetic sequence 600, the new lexical annotators 422 and parsing rule annotators 432 are saved and used (e.g., in a UIMA pipeline) to search through genetic sequences to find matches to the new rules. Continuing with the example genetic sequence 600, the analysis engine 410 locates the combination of: SequenceR A SequenceG. FIG. 9 illustrates the matched pattern 902 in an example genetic sequence 600 in accordance with certain embodiments.

Figure 10:
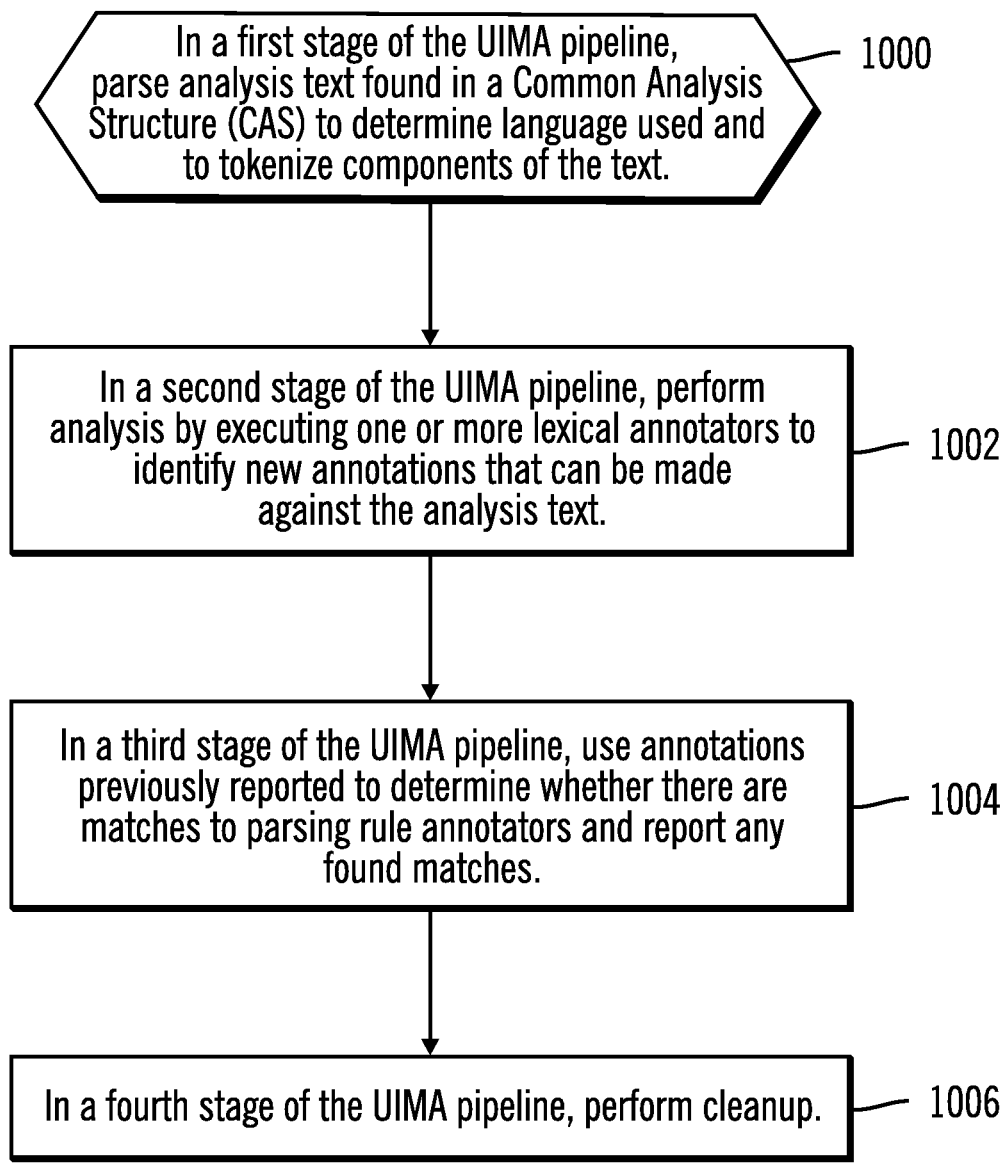
FIG. 10 illustrates, in a flow diagram, operations performed to locate a genome pattern in analysis text using Unstructured Information Management Architecture (UIMA) pipeline in accordance with certain embodiments.

FIG. 10 illustrates, in a flow diagram, operations performed to locate a genome pattern in analysis text using a UIMA pipeline in accordance with certain embodiments. Control begins at block 1000, in a first stage of the UIMA pipeline, analysis text found in a Common Analysis Structure (CAS) is parsed to determine language used and to tokenize components of the text (e.g., natural language text). The CAS may be described as a common data structure shared by UIMA framework components encapsulating analysis results shared across the various UIMA components. In the example genetic sequence 600, the language used does not matter and may default to English. Because the text is a sequence of nucleotide character representations, the tokenization annotates each nucleotide as an individual token. FIG. 11 illustrates a logical representation of the CAS 1100 after this first UIMA stage in accordance with certain embodiments.

In block 1002, in a second stage of the UIMA pipeline, analysis is performed by executing one or more lexical annotators 422 to identify new annotations that can be made against the analysis text. In this second stage, SequenceG and SequenceR annotations are added to the CAS. FIG. 12 illustrates a logical representation of the CAS 1200 after this second UIMA stage in accordance with certain embodiments.

In block 1004, in a third stage of the UIMA pipeline, annotations previously reported are used to determine whether there are matches to parsing rule annotators and any found matches are reported. That is, the third logical stage of the UIMA pipeline is to work through the parsing rule annotators. Continuing with the example genetic sequence 600, a single parsing rule was created, called the "SequenceRAG" parsing rule. Using the annotations already created in the previous stages of the UIMA pipeline, the analysis engine 410 uses the parsing rule to determine whether there are any "matches" based on the parsing rule definition. As a reminder, the parsing rule is looking for any SequenceR annotations followed immediately by an "A" token, followed immediately by a SequenceG annotation. FIG. 13 illustrates a logical representation of the CAS 1300 after this third UIMA stage in accordance with certain embodiments.

In block 1006, in a fourth stage of the UIMA pipeline, cleanup is performed. The UIMA cleanup stage is used to do any cleanup work needed on the CAS that has been generated and populated thus far in the process. Continuing with the example, nothing is required in this stage. The CAS remains the same. FIG. 14 illustrates a logical representation of the CAS 1400 after this fourth UIMA stage in accordance with certain embodiments.

In certain embodiments, a "CAS consumer" may be described as any component in the UIMA framework that uses the CAS for information. There are two main consumers of the CAS: each successive stage in the UIMA pipeline and the final consumer at the end of the pipeline. When the UIMA pipeline is constructed, each successive stage, after the first, uses the CAS to determine whether additional annotations are added or removed from the CAS. Consumers downstream see these modifications and do not need to reparse the natural language text. The final CAS consumer is generally some computer process that "reads" which annotations have been located in the natural language text and "acts" on this. This can initiate additional processing or it can be as simple as reporting the information to some interface (e.g., a graphical user interface).

Continuing with the example genetic sequence 600, the final CAS consumer may inspect the annotations to see whether any of the SequenceRAG annotations have been found, and, if so, highlight that portion of the original natural language text with bolded and colored font so that it can stand out from the rest of the nucleotide sequence on a computer monitor. FIG. 15 illustrates the matched pattern 1502 in an example genetic sequence 600 in accordance with certain embodiments. In FIG. 15, the match is highlighted by displaying the characters in the match in bold and underlined. In various embodiments, the highlighting may take a different form.

Embodiments use analytics software to help aid research efforts in areas of genomic sequencing and genome annotation.

Embodiments attempt to reduce the resource costs involved in such genomic research are high, whether measuring time, effort, or money, while proving another tool for use in the sequencing and gene discovery efforts.

Embodiments use UIMA and custom-built annotators to aid in genome sequence research. Thus, embodiments provide techniques in which custom UIMA annotators are used to help continue genomic discovery while reducing resource costs and requirements.

In certain embodiments, the analysis engine 410 is text analytics software. Embodiments use text analytics software and a UIMA framework for facilitating research efforts in the area of genomic sequencing and genomic annotations.

The text analytics software has the ability of annotating textual data based on rules, patterns, and other UIMA based analytic packages. The genome is a composed out of a series of chromosomes—genes that are represented by a sequence of characters A G C T that have certain significance in terms of genes presence. The researcher in the genome area us looking for specific sequences with biological meaning.

The UIMA framework is intended to be used to help users extract additional information out of unstructured text based on the knowledge of the way a particular language's grammar is constructed and the linguistic "rules" that are commonly followed in communicating in that language, etc. In embodiments, the use of UIMA focuses on the use of UIMA to locate sequences of characters (genome information) and the relationships that may be discovered via loose parsing rules developed around these sequences.

Embodiments provide a genomics research tool capable of locating various sequences of nucleotides and whatever relationship the researcher desires to look for.

Thus, embodiments use annotations and customized rules to find patterns in genetic sequences. Embodiments find sub-sequences (from a genetic sequence) based upon proximity, order, and other rules.

Additional Embodiment Details

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, an application specific integrated circuit (ASIC), a random access memory (RAM), a read-only memory (ROM), an erasable programmable read-only memory (EPROM or Flash memory), an optical fiber, a portable compact disc read-only memory (CD-ROM), an optical storage device, a magnetic storage device, solid state memory, magnetic tape or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the embodiments of the invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational processing (e.g., operations or steps) to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The code implementing the described operations may further be implemented in hardware logic or circuitry (e.g., an integrated circuit chip, Programmable Gate Array (PGA), Application Specific Integrated Circuit (ASIC), etc. The hardware logic may be coupled to a processor to perform operations.

Devices that are in communication with each other need not be in continuous communication with each other, unless expressly specified otherwise. In addition, devices that are in communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the present invention need not include the device itself.

The illustrated operations of flow diagrams show certain events occurring in a certain order. In alternative embodiments, certain operations may be performed in a different order, modified or removed. Moreover, operations may be added to the above described logic and still conform to the described embodiments. Further, operations described herein may occur sequentially or certain operations may be processed in parallel. Yet further, operations may be performed by a single processing unit or by distributed processing units.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The terms "an embodiment", "embodiment", "embodiments", "the embodiment", "the embodiments", "one or more embodiments", "some embodiments", and "one embodiment" mean "one or more (but not all) embodiments of the present invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The corresponding structures, materials, acts, and equivalents of all means or step plus function elements in the claims below are intended to include any structure, material, or act for performing the function in combination with other claimed elements as specifically claimed. The description of embodiments of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The foregoing description of embodiments of the invention has been presented for the purposes of illustration and description. It is not intended to be exhaustive or to limit the embodiments to the precise form disclosed. Many modifications and variations are possible in light of the above teaching. It is intended that the scope of the embodiments be limited not by this detailed description, but rather by the claims appended hereto. The above specification, examples and data provide a complete description of the manufacture and use of the composition of the embodiments. Since many embodiments may be made without departing from the spirit and scope of the invention, the embodiments reside in the claims hereinafter appended or any subsequently-filed claims, and their equivalents.

The invention claimed is:

1. A computer system for locating a genome pattern, comprising:
a processor; and
a storage device connected to the processor, wherein the storage device has stored thereon a program, and wherein the processor is configured to execute instructions of the program to perform operations, wherein the operations comprise:
creating one or more lexical annotators that each identify a sequence of nucleotides of nucleotide bases selected from A, C, G, and T;
providing (1) the one or more lexical annotators, (2) one or more dictionary entries, (3) one or more previously-defined parsing rule annotators, and (4) one or more characters that each represent a nucleotide;
creating a parsing rule annotator that identifies an order of and a combination of at least two elements selected from (1) the one or more lexical annotators, (2) the one or more dictionary entries, (3) the one or more previously-defined parsing rule annotators, and (4) the one or more characters that each represent a nucleotide; and
creating an Unstructured Information Management Architecture (UIMA) pipeline to locate the genome pattern using the parsing rule annotator by:
in a first stage of the UIMA pipeline, parsing a genetic sequence that is found in a Common Analysis Structure (CAS) to determine a language used and to generate tokens that are added to the CAS with a start position and an end position for each of the tokens;
in a second stage of the UIMA pipeline, executing the one or more lexical annotators against the genetic sequence to identify one or more lexical annotations that are added to the CAS with a start position and an end position for each of the one or more lexical annotations; and
in a third stage of the UIMA pipeline, using the start position and the end position for each of the tokens and the start position and the end position for each of the one or more lexical annotations to identify a match to the parsing rule annotation and to form a new annotation that is added to the CAS.

2. The computer system of claim 1, wherein the parsing rule annotator includes lexical annotators and no previously-defined parsing rule annotators.

3. The computer system of claim 1, wherein the parsing rule annotator includes previously-defined parsing rule annotators and no lexical annotators.

4. The computer system of claim 1, wherein a Software as a Service (SaaS) is provided to perform the system operations.

5. The computer system of claim 1, wherein there are multiple occurrences of a same lexical annotation with different start positions and end positions.

6. The computer system of claim 1, wherein the operations further comprise:
in response to determining that any token matches to a dictionary entry from the one or more dictionary entries, storing a new annotation in the CAS.

7. The computer system of claim 1, wherein each of the one or more dictionary entries represents a feature of a human.

8. A computer program product for locating a genome pattern, the computer program product comprising:
a computer readable storage medium having computer readable program code embodied therewith, wherein the computer readable program code, when executed by a processor of a computer, is configured to perform:
creating one or more lexical annotators that each identify a sequence of nucleotides of nucleotide bases selected from A, C, G, and T;
providing (1) the one or more lexical annotators, (2) one or more dictionary entries, (3) one or more previously-defined parsing rule annotators, and (4) one or more characters that each represent a nucleotide;
creating a parsing rule annotator that identifies an order of and a combination of at least two elements selected from (1) the one or more lexical annotators and (2) the one or more dictionary entries, (3) the one or more previously-defined parsing rule annotators, and (4) the one or more characters that each represent a nucleotide; and
creating an Unstructured Information Management Architecture (UIMA) pipeline to locate the genome pattern using the parsing rule annotator by:
in a first stage of the UIMA pipeline, parsing a genetic sequence that is found in a Common Analysis Structure (CAS) to determine a language used and to generate tokens that are added to the CAS with a start position and an end position for each of the tokens;
in a second stage of the UIMA pipeline, executing the one or more lexical annotators against the genetic sequence to identify one or more lexical annotations that are added to the CAS with a start position and an end position for each of the one or more lexical annotations; and
in a third stage of the UIMA pipeline, using the start position and the end position for each of the tokens and the start position and the end position for each of the one or more lexical annotations to identify a match to the parsing rule annotation and to form a new annotation that is added to the CAS.

9. The computer program product of claim 8, wherein the parsing rule annotator includes lexical annotators and no previously-defined parsing rule annotators.

10. The computer program product of claim 8, wherein the parsing rule annotator includes previously-defined parsing rule annotators and no lexical annotators.

11. The computer program product of claim 8, wherein a Software as a Service (SaaS) is configured to perform the computer program product operations.

12. The computer program product of claim 8, wherein there are multiple occurrences of a same lexical annotation with different start positions and end positions.

13. The computer program product of claim 8, wherein the computer readable program code, when executed by the processor of the computer, is configured to perform:
   in response to determining that any token matches to a dictionary entry from the one or more dictionary entries, storing a new annotation in the CAS.

14. The computer program product of claim 8, wherein each of the one or more dictionary entries represents a feature of a human.

\* \* \* \* \*